United States Patent [19]

Funakoshi et al.

[11] Patent Number: 5,051,526
[45] Date of Patent: Sep. 24, 1991

[54] BENZHYDRYLAMINE DERIVATIVES

[75] Inventors: Susumu Funakoshi, Kyoto; Eigoro Murayama, Shizuoka, both of Japan

[73] Assignee: Chugai Seiyaku Kabushiki Kaisha, Tokyo, Japan

[21] Appl. No.: 527,806

[22] Filed: May 24, 1990

Related U.S. Application Data

[62] Division of Ser. No. 316,167, Feb. 27, 1989, Pat. No. 4,965,405.

[30] Foreign Application Priority Data

Feb. 29, 1988 [JP] Japan .................................. 1-46710

[51] Int. Cl.$^5$ ............................................ C07C 271/22
[52] U.S. Cl. ..................................... 560/27; 530/309; 530/315; 530/334; 562/441
[58] Field of Search ........................... 560/27; 562/441

[56] References Cited

PUBLICATIONS

Oe et al., Chemical Abstracts, vol. 81, 120462w, (1974).
Albericio et al., Internat'l Journal of Peptide & Protein Res., vol. 30, 1987, pp. 206-216.
Funakoshi et al., Journal of the Chemical Soc., Chem. Commun., vol. 5, Mar. 1, 1988, pp. 382-384.

Primary Examiner—José G. Dees
Assistant Examiner—Vera C. Clarke
Attorney, Agent, or Firm—Browdy and Neimark

[57] ABSTRACT

Novel benzhydrylamine derivatives represented by general formulas (I) and (II) are useful as reaction reagents for the solid-phase synthesis of polypeptide amides making use of 9-fluorenylmethyloxycarbonyl group ("Fmoc"). An intermediate for these derivatives represented by the general formula (III) is also disclosed:

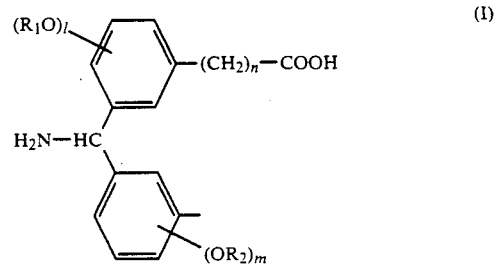

(I)

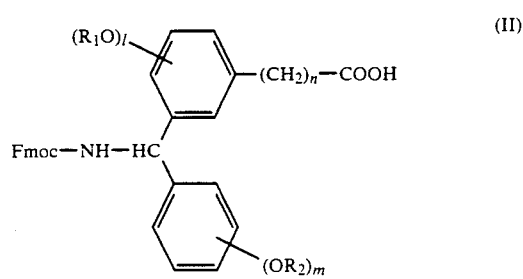

(II)

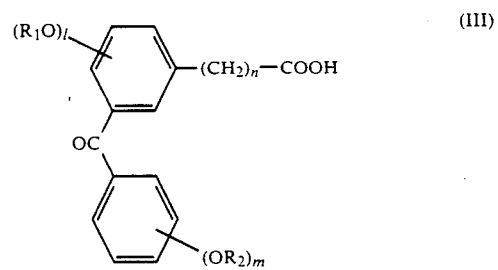

(III)

where $R_1$ and $R_2$ each independently represents a $C_{1-3}$ lower alkyl; n is an integer of 1–4; l is 1 or 2; and m is 1 or 2.

1 Claim, No Drawings

BENZHYDRYLAMINE DERIVATIVES

This is a division of application Ser. No. 07/316,167 filed Feb. 27, 1989, now U.S. Pat. No. 4,965,405.

BACKGROUND OF THE INVENTION:

The present invention relates to novel benzhydrylamine derivatives that are useful as reaction reagents for the solid-phase synthesis of polypeptide amides making use of a 9-fluorenylmethyloxycarbonyl group (hereinafter abbreviated as "Fmoc"). The present invention also relates to an intermediate of such derivatives.

The use of Fmoc, which is the base-labile protecting group developed by Carpino and Han, in the automated solid-phase synthesis of polypeptides has been known in the art (Carptino, L. A., Han, G. Y.: J. Am. Chem. Soc., 92, 5748 (1970); Carpino, L. A.: Acc. Chem. Res., 20, 401 (1987)). This method employs, in combination with Fmoc, a t-butoxycarbonyl (hereinafter abbreviated as "Boc") or t-butyl (hereinafter abbreviated as "tBu") ester or ether as an acid-labile group for protecting side chains in amino acids. Protecting groups such as Boc and tBu can be cleaved in the final step of the solid-phase synthesis by mild treatment with trifluoroacetic acid (hereinafter abbreviated as "TFA"). In the solid-phase synthesis by this method, UV absorption spectra makes it possible to monitor the progress of reactions, i.e., the elimination of protecting groups for α-nitrogen in amino acids on a polymer support. This Fmoc-based strategy has made the synthesis of methionine- or cystein-containing polypeptides easier than before; as it has the synthesis of acid-sensitive tryptophan-containing polypeptides.

However, the procedure for the preparation of polypeptide amide by Fmoc strategy seems not to be well established, since in this approach, it is necessary to explore precursors of the amide function, preferably more acid-labile precursors than those hitherto employed in the Merrifield's solid-phase synthesis. At present, several resins coupled to benzylamine or benzhydrylamine have been introduced for this purpose. However, in order to prepare these resins, difficult-to-handle chloromethylated polystyrene resin has to be manipulated. In comparison with such laborious manipulation, the use of a handle-reagent, which can be directly introduced onto the commercially available polystyrene resin, is attractive from a practical viewpoint. As such a candidate, Albericio and Barnary introduced a modified benzylamine reagent, 5-[(2' or 4')-Fmoc-aminomethyl-3', 5'-dimethoxy] phenoxyvaleric acid (Albericio, F., Barnary, G.: Int. J. Peptide Protein Res., 30, 206 (1987))

However, this reagent involves two problems: one is that the material can be obtained through seven steps from the starting material, and the other is that the overall yield of the product is only 15%.

The inventors of the present invention conducted intensive studies in order to solve the above-described problems and found the following: by introducing a lower alkoxy group to both benzene rings in benzhydrylamine, the C—N linkage in benzhydrylamine is rendered acid-labile; by attaching a certain group such as a propionic acid group to benzhydrylamine, the latter could be effectively coupled to an aminomethylated polystyrene resin. The present invention has been accomplished on the basis of these observations.

The present invention provides novel benzhydrylamine derivatives of the following general formulas (I) and (II) which are useful as reaction reagents that are capable of efficient solid-phase synthesis of polypeptide amides. The present invention also provides a novel benzophenone derivative as an intermediate of these derivatives which is represented by the following general formula (III):

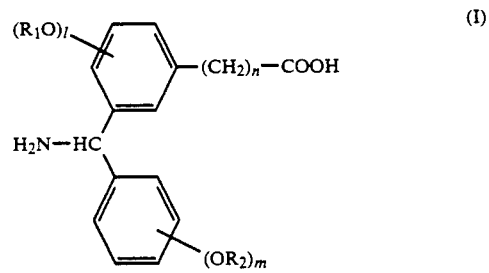

(where $R_1$ and $R_2$ each independently represents a $C_{1-3}$ lower alkyl; n is an integer of 1–4; l is 1 or 2, and m is 1 or 2);

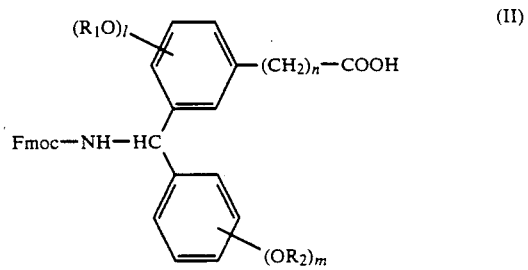

(where $R_1$, $R_2$, n, l and m have the same meanings as defined above; and Fmoc is a 9-fluorenylmethyloxycarbonyl group); and

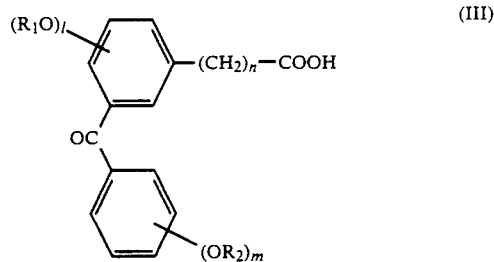

(where $R_1$, $R_2$, n, l and m have the same meanings as defined above).

Compounds of the general formula (I), (II) and (III) may be prepared by the following sequence of reactions, for example, starting with methyl 3-(4-methoxyphenyl)propionate:

1) Friedel-Crafts' condensation of methyl 3-(4-methoxyphenyl)propionate and p-methoxybenzoyl chloride;

2) Saponification of the resulting methyl ester;

3) Treatment with hydroxylamine (production of oxime);

4) Reduction of the resulting oxime with Zn (in acetic acid); and

5) Attachment of Fmoc to the resulting amino compound by treatment with Fmoc-OSu (Su stands for N-hydroxysuccinimidyl).

The resulting Fmoc reagent is loaded on an aminomethylated polystyrene resin by condensation with dicyclohexylcarbodiimide (hereinafter abbreviated as "DCC") in the presence of 1-hydroxybenzotriazole (hereinafter abbreviated as "HOBt"). This reaction is continued until the resin becomes negative to a Kaiser test. Before using the resin as a reaction agent, the Fmoc group attached is removed by treatment with dimethylformamide (hereinafter abbreviated as "DMF") containing 20% piperidine. Thus, 2,4'-dimethoxybenzhydrylamine resin anchored through the propionyl linkage (hereinafter named "Resin A") is readily prepared.

In addition, the Fmoc reagent is condensed onto an amino acid, for example, Ile which is bound to a PAM resin (PAM is the acronym for 2-phenylacetamidemethyl), then the Fmoc group is removed as described above to produce another resin for Fmoc-based solid-phase synthesis (hereinafter named "Resin B"). In this resin, the amino acid (e.g. Ile) used serves to monitor the amount in which the polypeptide amide is liberated by acid hydrolysis.

Methods of synthesizing the compounds of the present invention, as well as Resins A and B which are reaction reagents containing those compounds are described hereinafter in detail with reference to working examples. In order to identify the respective compounds, chromatography, NMR, MS and IR analyses were conducted with the following apparatus: Chromatography: Using a thin layer of silica gel (Kiesel-gel G, Merck), chromatography was conducted [$Rf_1$, $CHCl_3$; $Rf_2$, $CHCl_3$-MeOH-$H_2O$ (8:3:1)].

Nuclear magnetic resonance ($^1$H-NMR) spectra: Taken on a JEOL FX-200 spectrometer, with tetramethylsilane used as an internal standard.

Mass spectra (MS): Taken on a JEOL JMS-01SG-2 spectrometer.

Infrared (IR) absorption: Measured with a Hitachi 215 spectrophotmeter.

EXAMPLE 1

Synthesis of methyl 3-(4-methoxyphenyl)propionate (Documented Substance)

Thionyl chloride (3.1 ml, 42.5 mmol) was added slowly to methanol (30 ml) with stirring under cooling with a Dry Ice/methanol bath. After allowing the reaction to warm to room temperature, 3-(4-methoxyphenyl) propionic acid (5 g, 27.7 mmol) was added and stirred for an additional 1 hour. The solvent was removed in vacuo and the residue was dissolved in ethyl acetate. The solution was washed twice with a saturated aqueous solution of sodium bicarbonate, then once with a saturated aqueous solution of sodium chloride. After drying over unhydrous sodium sulfate, the solvent was evaporated in vacuo to produce a pale yellow crystal in an amount of 5.29 g (yield, 98%).

$Rf_1$: 0.83

EXAMPLE 2

Synthesis of methyl 3-(4-methoxybenzoyl)-4-methoxyphenylpropionate

The methyl 3-(4-methoxyphenyl)propionate (10.8 g, 55.6 mmol) prepared in Example 1 and 4-methoxybenzoyl chloride (11.4 g, 66.8 mmol) were dissolved in nitrobenzene (200 ml). To the ice-chilled solution, $AlCl_3$ (26.7 g, 200.3 mmol) was added in 6 portions with vigorous stirring over a period of 3 hours. After all portions of $AlCl_3$ were added, stirring was continued for an additional 1 hour. The reaction mixture was poured into a beaker containing a mixture of ice and 120 ml of 1N CHl and stirred vigorously. The mixture was transferred into a separating funnel, which was shaken well after the addition of ethyl acetate. The organic layer in the solution was washed twice with a saturated aqueous solution of sodium bicarbonate, then twice with a saturated aqueous solution of sodium chloride. After drying over unhydrous sodium sulfate, the solvent was removed in vacuo. The residue was purified by flash column chromatography using 30% ethyl acetate/hexane to produce a pale yellow oil.

Yield: 17.8 g (97%)

$Rf_1$: 0.14

MS: 328.1306 (cal'd for $C_{19}H_{20}O_5$: 328.1310)

NMR ($CDCl_3$): δ 2.61 (t, J=7.8 Hz, 2H), 2.92 (t, J=7.8 Hz, 2H), 3.66 (s, 3H), 3.71 (s, 3H), 3.86 (s, 3H), 6.91 (dt, J=9.0 and 2.3 Hz, 2H), 6.91 (d, J=8.5 Hz, 1H), 7.14 (d, J=2.2 Hz, 1H), 7.28 (dd, J=8.5 and 2.2 Hz, 1H), 7.79 (dt, J=9.0 and 2.3 Hz, 2H).

IR(neat): Vmax 2920, 1724, 1648, 1590, 1492, 1416, 1300, 1250, 1162, 1022, 840 $cm^{-1}$.

EXAMPLE 3

Synthesis of Ketoxime

The ketone (17.3 g, 52.7 mmol) prepared in Example 2 was dissolved in methanol (130 ml) and water (20 ml). To the ice-chilled solution, tablets of sodium hydroxide (5.0 g, 125 ml) were added with stirring and the mixture was allowed to warm to room temperature. The reaction mixture was stirred at room temperature for an additional 1 hour until the ester was completely hydrolyzed. The resulting acid solution ($Rf_2$, 0.84) was ice-chilled again, then sodium hydroxide (13.8 g, 345 mmol) and hydroxylamine hydrochloride (33.0 g, 474 mmol) were added to the mixture, and refluxed for 6 hours. After completion of the reaction, methanol in the reaction solution was evaporated in vacuo. A small amount of water was added to the residue, the resulting suspension was made acidic with citric acid and extracted 5 times with ethyl acetate. The extracted organic layers were combined, washed twice with a saturated aqueous solution of sodium chloride and dried over unhydrous sodium sulfate, followed by distilling off the solvent. The residue was recrystallized from ethyl acetate and n-hexane to produce a colorless needle.

Yield: 15.2 g (88%)

mp: 177°–178° C.

$Rf_2$: 0.75

NMR ($CD_3OD$): δ2.59 (t, J=7.4 Hz, 2H), 2.89 (t, J=7.4 Hz, 2H), 3.57 (s, 3H), 3.79 (s, 3H), 6.85 (dt, J=9.0 and 2.4 Hz, 2H), 6.90 (d, J=8.3 Hz, 1H), 7.16 (d, J=2.4 Hz, 1H), 7.25 (dd, J=8.3 and 2.4 Hz, 1H), 7.52 (dt, J=9.0 and 2.4 Hz, 2H).

IR(KBr): Vmax 3170, 2995, 1702, 1602, 1512, 1420, 1248, 1178, 1021, 952, 830 $cm^{-1}$.

| Elemental analysis for $C_{18}H_9NO_5$ (329.4): | | |
|---|---|---|
| C | H | N |
| Cal'd 65.64% | 5.81% | 4.25% |
| Found 65.66% | 5.84% | 4.26% |

EXAMPLE 4

Synthesis of 3-(α-amino-4-methoxybenzyl)-4-methoxyphenylpropionic acid (Compound of the Present Invention)

The ketoxime (5.0 g, 15.2 mmol) prepared in Example 3 was dissolved in acetic acid (140 ml) and zinc (10 g) which was washed with 0.02 N HCl for 5 min, then with water, was slowly added to the solution while being cooled with ice.

After stirring for 1 hour, the mixture was subjected to filtration through Celite. The acetic acid in the filtrate was evaporated in vacuo and ethyl acetate was added to the residue, thereby allowing the product to crystallize. After standing overnight, the crystal was collected by filtration and the resulting powder was recrystallized from ethanol to give a white powder.

Yield: 3.84 g (80%)
Rf$_2$: 0.38
mp: 191.5°–192.5° C.
NMR (CD$_3$OD): δ 2.41 (t, J=6.8 Hz, 2H), 2.85 (t, J=6.8 Hz, 2H), 3.78 (s, 6H), 5.63 (s, 1H), 6.88–6.98 (m, 1H), 6.93 (d, J=8.7 Hz, 2H), 7.12–7.32 (m, 2H), 7.29 (d, J=8.7 Hz, 2H).
IR (KBr): νmax 3640, 3370, 2945, 1635, 1610, 1565, 1532, 1510, 1400, 1245, 1034 cm$^{-1}$.
MS: 315.1476 (cal'd for C$_{18}$H$_{21}$NO$_4$: 315.1470)

| Elemental analysis for C$_{18}$H$_{21}$NO$_4$.1.5H$_2$O (342.4): | | | |
|---|---|---|---|
| | C | H | N |
| Cal'd | 63.14% | 7.06% | 4.09% |
| Found: | 63.38% | 7.04% | 3.88% |

The synthetic route to a compound of the present invention, 3-(α-amino-4-methoxybenzyl)-4-methoxyphenylpropionic acid, from the starting material 3-(4-methoxyphenyl)propionic acid is represented by structural formulas as follows:

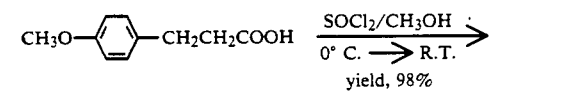

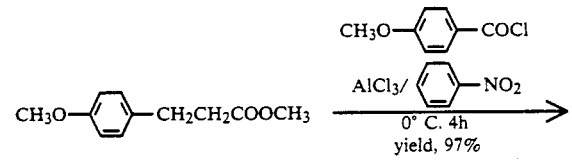

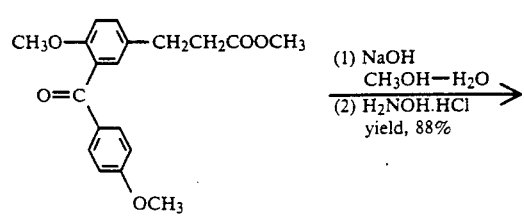

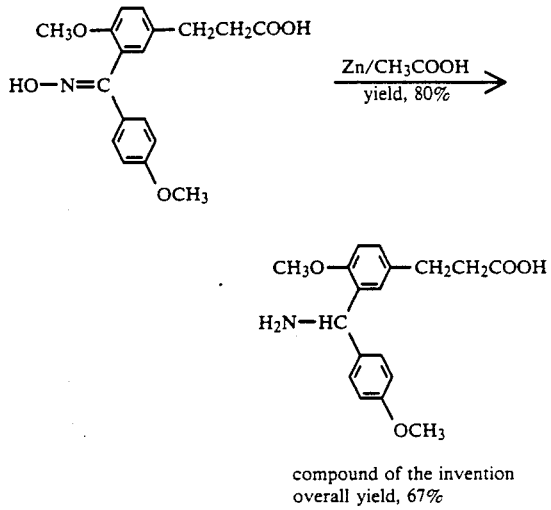

compound of the invention
overall yield, 67%

Using the compound of the present invention shown above, 3-(α-Fmoc-amino-4-methoxybenzyl)-4-methoxyphenylpropionic acid was synthesized as described below, and Resins A and B, both being an amide precursor resin, were produced using this propionic acid derivative.

EXAMPLE 5

Synthesis of 3-(α-Fmoc-amino-4-methoxybenzyl)-4-methoxyphenylpropionic acid

The 3-(α-amino-4-methoxybenzyl)-4-methoxyphenylpropionic acid (1.0 g, 3.17 mmol) prepared in Example 4 was dissolved in 5 ml of DMF containing triethylamine (0.88 ml). To the solution, 1.28 g of Fmoc-OSu was added and the mixture was stirred at room temperature for 1 hour. The solvent was evaporated in vacuo and 5% citric acid and ether were added to the residue. The resulting power was recrystallized from methanol and ether.

Yield: 1.70 g (100%) mp: 174°–175° C. Rf$_2$: 0.73

| Elemental analysis for C$_{33}$H$_{31}$NO$_6$ (537.6): | | | |
|---|---|---|---|
| | C | H | N |
| Cal'd | 73.72% | 5.81% | 2.61% |
| Found | 73.47% | 5.83% | 2.59% |

EXAMPLE 6

Preparation of NH$_2$-DMBH-CH$_2$CH$_2$-CO-aminomethylpolystyrene resin (Resin A)

DCC (326 mg) and HOBt (243 mg) were added to a DMF solution of the acid (774 mg, 1.44 mmol) prepared in Example 5, and the resulting mixture was stirred at room temperature for 1 hour, and filtrated. The filtrate was mixed with an aminomethylpolystyrene resin (1 g, amino content 0.72 mmol/g) prewashed with DMF and the suspension was gently shaken for 10 hours until the resin became negative to a Kaiser test. In order to mask the amino function completely, the resin was further treated with 29% Ac$_2$O in DMF (20 ml) for 1 hour. The resin was washed with DMF, then with CH$_2$Cl$_2$ (two times each) and dried in vacuo; yield 1.28 g. Before use in the synthesis of polypeptide amide, the resin thus prepared was treated with 20% piperidine in DMF (5 ml/200 mg resin) for 5 min. This treatment was repeated once more (15 min) and the resin was washed with DMF (5 ml ×5).

min. The same treatment was conducted once more for 15 min and the treated resin was washed with DMF (5 ml×5).

The route of synthesis of resins A and B from the compound of the present invention shown above may be represented by structural formulas as follows:

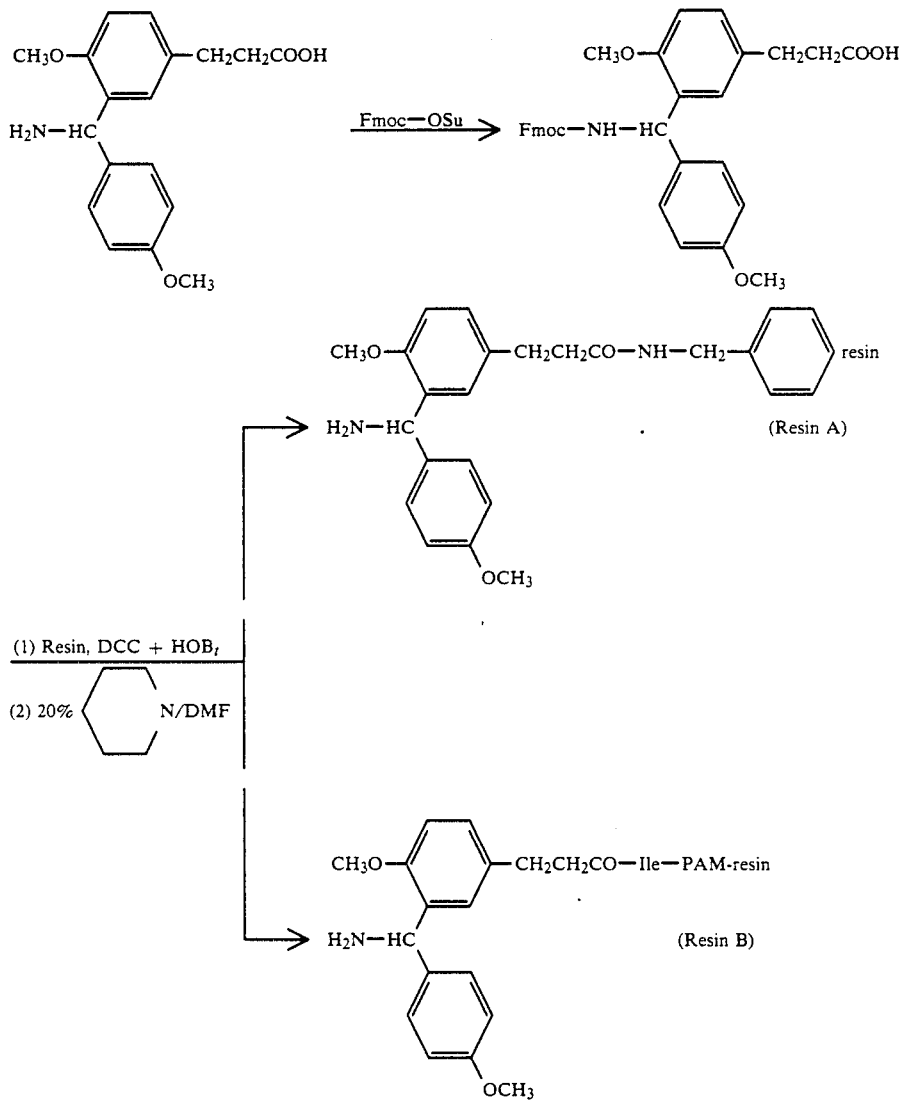

EXAMPLE 7

Preparation of NH2-DMBH-CH2CH2-CO-Ile-PAM-polystyrene resin (Resin B)

The acid (269 mg, 0.5 mmol) prepared in Example 5 was dissolved in DMF (5 ml) and the solution was mixed with DCC (103 mg) and HOBt (77 mg). The mixture was stirred at room temperature for 1 hour and filtered. The filtrate was mixed with H-Ile-PAM-polystyrene resin (139 mg, Ile content 0.76 mmol/g prewashed with DMF and the suspension was shaken for 3 hours until the resin became negative to a Kaiser test. The resin was washed with DMF and further treated with 20% Ac2O/DMF (5 ml) for 1 hour. The treated resin was washed with DMF, then with CH2Cl2 (3 times each) and dried in vacuo; yield 185 mg. Before use in the synthesis of polypeptide amide, the resin was treated with 20% piperidine/DMF (5 ml/200 mg resin) for 5

The characteristics of the resins thus prepared were examined using Fmoc-amino acid. Described below is the case where phenylalanine was cleaved from resin B.

TEST EXAMPLE

Cleavage of H-Phe-NH2 from the Resin B

Fmoc-Phe-OPfp (0.5 mmol) and HOBt (0.5 mmol) were added to a suspension of resin B (prepared from 185 mg, 0.1 mmol of the Fmoc-derivative) in DMF (5 ml) and the mixture was shaken for 1 hour. The resin was successively washed with DMF (5 ml×5), then treated with 20% piperidine in DMF (5 ml) for 15 min. The treated resin was washed with DMF (5 ml×5) and CH2Cl2 (5 ml×5) and dried in vacuo; yield 179 mg. The dried resin (5 mg) was treated with 1 M thioanisole/TFA-m-cresole (100 μl−10 μl) at 28° C. for 60 min. H-Phe-NH2 liberated was determined by TLC scanner.

The latter treated resin was subjected to 6N HCl hydrolysis. No Phe was detected by amino acid analyser. This result shows that phenylalanine had been cleaved almost completely from the resin. It was therefore established that resin B is useful as an amide precursor for amino acids and that the thioanisole-containing solution described above is a superior cleavage reagent.

Next, the fact that resins containing the compound of the present invention are useful for the solid-phase synthesis of polypeptide amides was demonstrated by synthesizing three biologically active polypeptides.

Three physiologically active polypeptide amides were purified by high-performance liquid chromatography (here-under abbreviated as "HPLC") which was conducted with a Waters 204 compact model. The Fmoc-based solid-phase synthesis was carried out by the method of Atherton et al. (Atherton, E., Brown, E., Sheppard, R. C. : J. Chem. Soc., Chem. Commun., 1981, 1151).

PREPARATION EXAMPLE 1

Preparation of Tetragastrin, H-Trp-Met-Asp-Phe-NH$_2$

Starting with resin B (185 mg, 0.1 mmol), the Fmoc-based solid-phase synthesis was conducted according to the principle of Atherton et al.; Fmoc deprotection: treatment with 20% piperdine/DMF (5 ml, 5 min and 5 ml, 15 min) followed by washing with DMF (5 ml×5): Condensation by the Pfp esters of corresponding Fmoc amino acids in the presence of HOBt in DMF (5 ml) for 60 min at room temperature, followed by washing with DMF (5 ml×5). H-Trp-Met-Asp(OtBu)-Phe-resin B was obtained (239 mg); amino acid ratios in a 6 M HCl hydrolysate: Asp 1.12, Met+Met (O) 0.52, Phe 1.10, Trp N.d., Ile 1.00 (internal standard loaded on resin B).

The polypeptide resin thus obtained (100 mg, 41.8 μmol) was reacted with 1M thioanisole/TFA (5 ml) in the presence of EDT (1,2-ethanedithiol, 293 μl) and m-cresol (293 μl) at 28° C. for 1 hour. The resin was removed by filtration and washed with TFA. The filtrate and the washings were combined, then TFA was removed by evaporation in vacuo and dry ether was added to the residue. The resulting powder was collected by centrifugation and washed with ether; yield 14.9 mg. When the treated resin was subjected to 6N HCl hydrolysis, the ratio of Phe and Ile was 0.39:1.00, indicating that ca. 61 % of the peptide was cleaved off from the resin under the reaction conditions described above. The crude peptide thus obtained as purified by HPLC on a Cosmosil 5C18 column ST (4.6×150 mm) with a gradient elution of MeCN (10–60%, for 50 min) in 0.1% aqueous TFA at a flow rate of 1 ml/min (retention time 37.2 min, identical to that of synthetic tetragastrin); yield 10.2 mg (41%). Amino acid ratios in 4M MSA (methanesulfonic acid) hydrolysis: Asp 1.01, Met 0.72, Phe 1.00, Trp 0.82 (recovery of Phe, 76%).

PREPARATION EXAMPLE 2

Preparation of Neuromedin B

Starting with resin B (185 mg, amino content 0.1 mmol), H-Gly-Asn-Leu-Trp-Ala-Thr(tBu)-Gly-His(-Boc)-Phe-Met-resin B (291 mg) was synthesized by the Fmoc-based solid-phase synthesis according to the method mentioned above in Preparation Example 1.

The polypeptide resin (100 mg) was treated with 1M TMSBr(trimethylsilyl bromide)-thioanisole/TFA in the presence of EDT and m-cresol (295 μl, each) in an ice-bath for 1 hour. The resin was removed by filtration and washed with TFA (5 ml). The filtrate and the washings were combined, then TFA was removed by evaporation in vacuo and dry ether was added to the residue. The resulting powder was collected by centrifugation and lyophilized from 50% AcOH; yield 20.3 mg. Amino acid ratios of Ile and Phe in the treated resin were 1.00: 0.28, indicating that the cleavage yield was 72%. The crude product was purified by HPLC on a Cosmosil 5C18 ST column (4.6×150 mm) with a gradient of MeCN (10–60%, 50 min) in 0.1% aqueous TFA at a flow rate of 1 ml/min (the retention time 32.9 min, identical to that of an authentic sample of neuromedin B); yield 14.1 mg (36%, based on Met loaded on the resin). Amino acid ratios in a 4M MSA hydrolysate: Asp 1.07, Ser 1.03, Gly 2.17, Ala 1.15, Met 0.89, Leu 1.06, Phe 1.00, Trp 0.80 (recovery of Phe, 83%).

PREPARATION EXAMPLE 3

Preparation of Arginine(Arg)-Vasopressin

Starting with the resin B (185 mg, 0.1 mmol), H-Cys-(Acm)-Tyr(Bu)-Phe-Gln-Asn-Cys(Acm)-Pro-Arg(Mtr)-Gly-resin B (280 mg) was obtained by the Fmoc-based solid-phase synthesis according to the method mentioned in Preparation Example 1; (Acm=acetamidomethyl, and Mtr=4-methoxy-2,3,6-trimethylbenzenesulfonyl). Amino acid ratios of the peptide resin: Asp 0.84, Glu 0.83, Gly 1.00, Tyr 0.71, Pro 0.86, Phe 0.81, Arg 0.83.

This polypeptide resin (100 mg, 26.5 μmol) was suspended in TFA (5 ml) and reacted with Tl (CF$_3$COO)$_3$ (79.5 μmol) in the presence of anisole (0.5 ml) in an ice-bath for 60 min, then with TMSBr and thioanisole (to a concentration of 1M each) for an additional 60 min. The resin was washed with TFA (5 ml×3). The filtrate and the washings were combined and TFA and TMSBr were removed by evaporation in vacuo and the residue was treated with dry ether. The resulting powder was lyophilized from H$_2$O and purified by gel-filtration on Sephadex G-10 (1.8×70 cm), which was eluted with 0.2M AcOH. The desired fractions (3 ml, each, 21–35, monitored by UV absorption measurement at 280 nm) were combined and the solvent was removed by lyophilization to give a powder; yield 13.5 mg (45%, based on Gly loaded on the resin). This crude sample was further purified by HPLC on a Cosmosil 5C18 column (1.0×25 cm) with a gradient elution with MeCN (15–30%, 48 min) in 0.1% aqueous TFA at a flow rate of 1.8 ml per min (retention time 20.5 min, identical to that of an authentic sample of Argvasopressin); yield 8.8 mg (overall yield 30%, based on Gly loaded on the resin). Amino acid ratios in a 6N HCl hydrolysate: Asp 0.97, Glu 0.96, Gly 1.00, Cys 0.48, Tyr 0.89, Phe 0.97, Arg 0.90, Pro 0.90 (recovery of Gly, 100%).

The benzhydrylamine derivatives of the present invention offer the following advantages when resins containing them are used in the Fmoc-based solid-phase synthesis of polypeptide amides: first, the yield of polypeptide amides obtained is increased; secondly, the C—N linkage in the benzhydrylamine is more acid-labile than in the prior art, so the polypeptide obtained can be recovered efficiently from the support resin. For these advantages, the present invention holds much promise in making a substantial contribution to the art of producing physiologically active substances formed of polypeptide amides.

What is claimed is:

1. A benzhydrylamine derivative of the formula:

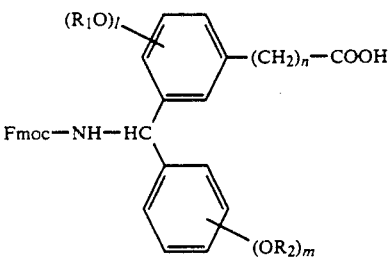
where $R_1$ and $R_2$ each independently represents a $C_{1-3}$ lower alkyl; n is an integer of 1-4; l is 1 or 2; m is 1 or 2; and Fmoc is a 9-fluorenylmethyloxycarbonyl group.
* * * * *